United States Patent [19]

Axelrod et al.

[11] Patent Number: 5,620,851
[45] Date of Patent: Apr. 15, 1997

[54] REPLICATIVE RNA-BASED AMPLIFICATION/DETECTION SYSTEMS

[75] Inventors: Vladimir D. Axelrod; Fred R. Kramer, both of New York, N.Y.; Paul M. Lizardi, Cuernavaca, Mexico; Donald R. Mills, Englewood, N.J.

[73] Assignee: The Trustees of Columbia University in the City of New York, New York, N.Y.

[21] Appl. No.: 323,631

[22] Filed: Oct. 17, 1994

Related U.S. Application Data

[63] Continuation of Ser. No. 908,833, Jul. 2, 1992, Pat. No. 5,356,774, which is a continuation of Ser. No. 241,624, Sep. 8, 1988, abandoned, which is a continuation-in-part of Ser. No. 191,450, May 9, 1988, abandoned, which is a continuation-in-part of Ser. No. 852,692, Apr. 16, 1986, Pat. No. 4,957,858.

[51] Int. Cl.$^6$ .......................... C07H 21/04; C07H 21/00; C12P 19/34; C12Q 1/68
[52] U.S. Cl. .................. 435/6; 435/4; 435/7.1; 435/15; 435/14; 435/91.21; 435/172.3; 435/320.1; 536/22.1; 536/24.1; 935/77; 935/78
[58] Field of Search .......................... 435/4, 6, 7.1, 15, 435/91.21, 14, 172.3, 320.1; 536/22.1, 24.1; 935/77, 78

[56] References Cited

U.S. PATENT DOCUMENTS 4,228,237 10/1980 Hevey et al. .
4,542,104 9/1985 Stryer et al. .
4,556,643 12/1985 Paau et a. .
4,683,195 7/1987 Mullis et al. .
4,683,202 7/1987 Mullis et al. .
4,711,955 12/1987 Ward et al. .
4,775,619 10/1988 Urdea et al. .
4,786,600 11/1988 Kramer et al. .
4,957,858 9/1990 Chu et al. .
5,356,774 10/1994 Axelrod et al. .............................. 435/6

FOREIGN PATENT DOCUMENTS 0128042 12/1984 European Pat. Off. .
0200362 12/1986 European Pat. Off. .
0201184 12/1986 European Pat. Off. .
2125964 3/1984 United Kingdom .
8706270 10/1987 WIPO .
8810315 12/1988 WIPO .
9002819 3/1990 WIPO .

OTHER PUBLICATIONS

Alagon, A.C. and King, T.P., Activation Of Polysaccharides With 2-Iminothiolane And Its Uses. Biochemistry, (1980) 19: 4341–4345.
Chu, B.C.F., et al., Synthesis Of An Amplifiable Reporter RNA For Bioassays. Nucleic Acids Research, (1986) 14: 5591–5603.
Chu, B.C.F. and Orger, L.E., Laboratory Methods: Detection of Specific DNA Sequences With Short Biotin–Labeled Probes. DNA, (1985) 4: 327–331.

(List continued on next page.)

Primary Examiner—W. Gary Jones
Assistant Examiner—Paul B. Tran
Attorney, Agent, or Firm—John P. White

[57] ABSTRACT

This invention relates to the use of functional reporter molecules in the detection and measurement of targets in a sample. The invention is predicated on the utilization of a transcription step between the production of an appropriate reporter molecule and replication based amplification in order to increase the number of detectable species as an indirect reference to target.

23 Claims, 1 Drawing Sheet

OTHER PUBLICATIONS

Chu, B.C.F. and Orgel, L.E., Ligation Of Oligonucleotides To Nucleic Acids Or Proteins Via Disulfide Bonds. Nucleic Acids Research, (1988) 16: 3671–3691.

Dreyer, G.B. and Deryan, P.B., Sequence–Specific Cleavage Of Single–Stranded DNA: Oligodexoynucleotide–EDTA–Fe (II). Proc. Natl. Acad. Sci. USA, (1985) 82: 968–972.

Forster, A.C., et al., Non–Radioactive Hybridization Probes Prepared By The Chemical Labeling Of DNA and RNA With A Novel–Reagent, Photobiotin. Nucleic Acids Research (1985) 13: 745–761.

Gillespie, et al., A Quantitative Assay For DNA–RNA Hybrids With DNA Immobilized On A Membrane. J. Mol. Biol. (1965) 12: 829–842.

Gordon, et al., The Surface Glycoproteins Of Human Skin Fibroblasts Detected After Electrophoresis By The Binding Of Peanut (Arachis Hypogae) Agglutinin And Castor–Bean Agglutinin I. Biochem. J. (1982) 208: 351–358.

Imam, A., et al., Generation And Immunohistological Characterization Of Human Monoclonal Antibodies To Mammary Carcinoma Cells. Cancer Research, (1985) 45: 263–271.

Kafatos, et al., Determination Of Nucleic Acid Sequence Homologies And Relative Concentration By A Dot Hybridization Procedure. Nuc. Acids Rec. (1979) 7: 1541–1552.

Kossel, et al., The Terminal Addition Of Riboadenylic Acid To Deoxyoligonucleotides By Terminal Deoxynucleotidyl Transferase As A Tool For The Specific Labeling Of Deoxyoligonucleotides At The 3'–Ends. Eur. J. Biochem. (1971) 22: 271–276.

Leary, et al., Rapid And Sensitive Colormetric Method for Visualizing Biotin–Labeled DNA Probes Hybridized To DNA Or RNA Immobilized On Nitrocellulose: Bio–Blots. Proc. Natl. Acad. Sci. (USA) (1983) 80: 4045–4059.

Melton,, D.A., et al., Efficient In Vitro Synthesis Of Biologically Active RNA and RNA Hybridization Probes From Plasmids Containing A Bacteriophage SP6 Promoter. Nucleic Acids Research (1984) 12: 7035–7056.

Miele, E.A., et al., Autocatalytic Replication Of A Recombinant RNA. J. Mol. Biol., (1983) 171: 281–295.

Miyake, T., et al., Grouping RNA Phages On The Template Specificity Of Their RNA Replicases. Proc. Natl. Acad. Sci. (USA) 68: 2022–2024.

Murasagi, et al., Biotin–Labeled Oligonucleotides: Enzymatic Synthesis And Use As Hybridization Probes. DNA (1984) 3: 269–277.

Saiki, R.K., et al., Enzymatic Amplification Of Beta–Globin Genomic Sequences And Restriction Site Analysis For Diagnosi Of Sickle Cell Anemia. Science, (1985) 230: 1350–1354.

Seibenlist, U., et al., E–Coli RNA Polymerase Interacts Homologously With Two Different Promoters. Cell (1980) 20: 269–281.

Stoflet, E.S., et al., Genomic Amplification With Transcript Sequencing, Science (1988) 239: 491–494.

FIGURE 1

REPLICATIVE RNA-BASED AMPLIFICATION/DETECTION SYSTEMS

This application is a continuation of U.S. Ser. No. 07/908,833, filed Jul. 2, 1992, now U.S. Pat. No. 5,356,774, issued Oct. 18, 1994. U.S. Ser. No.07/908,833 is a continuation of U.S. Ser. No. 241,624, filed Sep. 8, 1988, now abandoned, which is a continuation-in-part of U.S. Ser. No. 191,450, filed May 9, 1988, now abandoned, which is a continuation-in-part of U.S. Ser. No. 852,692, filed Apr. 16, 1986, now U.S. Pat. No. 4,957,858, issued Sep. 18, 1990, the contents of which are hereby incorporated by reference.

FIELD OF THE INVENTION

The present invention relates generally to advances in molecular biology and recombinant DNA technology.

More particularly, the present invention is directed to the methods and means, including assays and pharmaceutical kits containing requisite reagents and means, for detecting in an in vitro or ex vivo setting the presence of nucleic acid species, and by deduction the corresponding polypeptide that nucleic acid encodes, in a biological sample. The present invention makes use of replicative RNA for such detection and is predicated on the use of such replicative RNA to amplify by correspondence the segment of target nucleic acid or complement or hybridizing homologous segment. Thus, this invention relates particularly to reporter systems that employ RNAs that serve as templates for self-replication catalyzed by RNA-dependent RNA polymerases.

Among the applications in which the present invention finds use are in analyses of nucleic acid sequences characteristic of a particular or general pathogenic disease or condition by the in vitro or ex vivo nucleic acid probe hybridization assays of body fluids and tissues containing requisite target nucleic acid.

BACKGROUND OF THE INVENTION

It is a goal in this art to detect various nucleic acid sequences in a biological sample, in which the said sequences, as so-called target nucleic acid, is present in small amounts relative to its existence amongst a wide variety of other nucleic acid species including RNA, DNA or both. Thus, it is desirable to detect the nucleic acid encoding polypeptides that may be associated with pathological diseases or conditions, such as, for example, DNA correlating to that of the human immunodeficiency virus. In addition to the detection of nucleic acids encoding such viral particles, it is desirable to detect other nucleic acids characteristic of a pathological disease or condition such as a defective gene, as in the case of hemophilia, or in the detection of anti-pathogen antibodies of such diseases or conditions.

Characteristically, the nucleic acids associated with such are present, if at all, in very small amounts relative to total nucleic acid in a given biological sample, such as blood or other body fluid or tissue sample of a given individual to be tested.

Other important cases where the application of such technology finds use are detailed in said U.S. Ser. No. 852,692 and need not be repeated here.

The detection of such nucleic acid species requires such specificity that, if present, it is detectable and measurable from amongst the wide variety of other nucleic acid species with which it is environmentally associated. Some of these species may bear close homology, at least in isolated segments, with the target nucleic acid. Further, as noted above, these target nucleic acid species are very often found only in very minute amounts in the biological sample being tested. And yet, for proper diagnosis of the underlying disease state, it is essential that even small amounts of such target nucleic acid be detectable unequivocally for fidelity of the assay system.

Two fundamental approaches have been advanced for accomplishing the goal of the art. In one, the amount of nucleic acid in the sample is not altered or affected. Instead, a reporter system is developed whereby a large number of detectable molecules corresponding to the nucleic acid target are produced for ready detectability and measurement. Such a reporter system is a signal-generating system associated with the target nucleic acid producing a detectable signal representative of the number of molecules of target sequence. Such systems have employed a chromophore generating moiety linked to a oligonucleotide probe that hybridizes with the target nucleic acid sequence. The chromophore moiety can be isolated from those oligonucleotide probes that have properly hybridized to target, and measured. One such chromophore generating group is an enzyme such as alkaline phosphatase which has a chromogenic substrate producing under suitable conditions detectable and measurable colored molecules. Another such system employs radioactive labeling of the nucleic acid probe such that the signal generated by such properly hybridized target nucleic acid can be detected and measured.

A second approach has been developed that is fundamentally different in that it involves increasing the copy number of the target nucleic acid sequence itself, in particular in an amount greater than that of nucleic acid sequences with which it is associated in the sample. This can be done by selective amplification of the target nucleic acid sequence. One can refine the culture techniques of the sample such that somehow the target nucleic acid sequence is amplified preferentially to other nucleic acid sequences. These techniques are cumbersome and time consuming and subject to trial and error.

Another example of the second approach is amplification of a target nucleic acid sequence in a so-called "polymerase chain reaction" (PCR). This technique was reported by Saiki et al., *Science* 230, 1350 (1985) and Mullis et al., European Patent Application Publication Nos. 200362 and 201184 (See also U.S. Pat. Nos. 4,683,195 and 4,683,202), and particularly entails (1) hybridizing to a segment of target nucleic acid sequence a primer, (2) extending said primer with a polymerase, and (3) rendering single stranded the duplexes resulting from the chain extension reaction. This procedure can be repeated over a number of cycles so as to amplify the underlying target nucleic acid sequence. The procedure requires at least two nucleic acid probes and has three steps for a single cycle.

Certain RNAs are known to be susceptible to replication by certain polymerases, such as bacterial phage RNA-dependent RNA polymerase such as Qβ replicase and the replicase from brome mosaic virus (BMV). In this technique, the RNA can serve as a sequence template for replication by the RNA polymerase resulting in an amount of replicated RNA sequences that is an exponential increase of the amount initially present. See Miele et al., *J. Molecular Biology* 171, 281 (1983). A system in which probe for a target sequence is linked to an RNA capable of being replicated by Qβ replicase is described by Chu et al., *Nucleic Acids Research* 14, 5591 (1986) and by BMV replicase by March et al., *Positive Strand RNA Viruses*, Alan R. Liss (Publisher; New York) (1987; Proceedings of UCLA Symposium, 1986).

Until recently it has not been appreciated that (autocatalytic) replication could be employed to provide convenient, broadly applicable, highly sensitive reporter systems for analyses of nucleic acid sequences. Above-cited U.S. Ser. No. 852,692 provides the use of nucleic acid probe-replicative RNA adducts for use in detecting target nucleic acid sequences by amplification thereof via the exponential replicative process of the replicative RNA associated with the nucleotide probe. Thus, that invention combines the art of replication of RNA with the use of oligonucleotide hybridization probes to detect target nucleic acid by associated replicative amplification. Details of that invention can be readily adduced by reference to the co-pending patent application or its counterpart, published international application, both cited supra. One practical drawback of that method resides in its necessary use of relatively long, hence sensitive, sequences of replicatable RNA that may prove inherently unstable in the assay environment.

It is an object of the present invention to take further advantage of the basic replicative process for amplification, for ease in the detection of sequences corresponding to target nucleic acid sequences. It is a further object of the present invention to take advantage of other biological processes that serve in result to achieve amplification of a given nucleic acid sequence. In particular, advantage is taken of the natural transcription process (as the first step in expression of DNA to produce polypeptide products) whereby double-stranded nucleic acid templates containing a promoter sequence recognized by a DNA-dependent RNA polymerase is used to produce a plurality of corresponding RNA transcripts. Again, using this process, a large number of RNA transcripts can be produced,. that are themselves replicatable.

It is a further object of the present invention to combine the advantages of the replicative and transcript-producing procedures as a means for detecting and measuring corresponding target nucleic acid.

It is thus an object of the present invention to produce, in all events, a given RNA transcript sequence that corresponds by presence and amount to target nucleic acid sequence and that can be replicated to a plurality and that can be adapted by association with a signal grouping that is accountable for its detection and measurement.

It is thus an overall object of the present invention to meet the goals enumerated by the art and to overcome the disadvantages and problems encountered by prior researchers' endeavors. The present invention utilizes, if at all, only relatively short, hence stable, RNA sequences that need only contain a sequence that insures replicatability and nothing more. Thus, the present invention provides a straightforward technique that can be utilized with stable fidelity in an acceptably short period of time, employing the convenience of known reagents and having the precision necessary to reach consistent scientific results; one that can be employed in a reproducible assay setting and that is adaptable for use in kits for laboratory/clinical analyses. It is, hence, an object of the present invention to increase the detectability of certain nucleic acid sequences (target segments) by amplification of sequences associated with the presence of the target sequences in an in vitro or ex vivo system, utilizing the advantages provided by the natural transcription and replicative processes per se.

SUMMARY OF THE INVENTION

The present invention is predicated on the use of an oligonucleotide probe, suitable for hybridization with a segment of a target nucleic acid sequence, that has linked thereto a moiety that is capable of initiating the production of a plurality of RNA transcripts, themselves containing sequence operable for their multiple self-replication. The present invention thus employs novel adducts of covalently joined moieties, one an oligonucleotide probe capable of hybridizing with a target nucleic acid sequence and the other capable of initiating a transcription process producing a plurality of transcripts having the capability of self-replication.

In an embodiment, the present invention is directed to the novel adduct, its preparation and use, having linked moieties:

(1) an oligonucleotide probe capable of hybridizing to a target nucleic acid sequence in a sample containing same; and (2) a sequence comprising a promoter sequence operably linked to DNA encoding replicatable RNA that, when optionally cleaved away, is capable of producing replicatable RNA transcripts. The product RNA transcripts self-replicate with the aid of a suitable replicase and are then detected and measured in a manner known per se such as via incorporation of, or association with, a chromophore moiety or a radioactively detectable moiety, for example.

In all respects, the present invention is directed to the novel application of the natural principles of transcript production, and their replication, for the deduced detection and measurement of corresponding target nucleic acid sequence that may be present in a biological sample containing a mixture of nucleic acids including DNA, RNA or both.

The present invention is thus directed to all methods and means associated with the preparation and use of replicable RNA transcripts that can be amplified and detected as such and measured as a basis for the determination of the amount present, if any, of a corresponding target nucleic acid sequence. It is directed to their precursor adducts, that is, linked adducts of an oligonucleotide probe capable of hybridizing with said target nucleic acid sequence and a sequence comprising a promoter sequence operably linked to DNA encoding replicatable RNA. It is further directed to the preparation of such adducts and to their use in detecting by deduction a corresponding target nucleic acid sequence and measuring the amount of its presence in a given biological sample. The present invention is further directed to associated methods and means for devising assay systems based upon such adducts and their replicable transcript products and to kits incorporating such assay methodology together with the necessary reagents and means for measuring target nucleic acid sequences in a laboratory/clinical setting.

The present invention thus reduces to a method useful for the detection of at least one specific nucleic acid target sequence in a sample containing nucleic acid, comprising detecting a self-replicated RNA transcript, it being the product of transcription of a molecule containing DNA encoding said replicatable RNA transcript operably linked to a promoter therefor, said promoter and said DNA being a reporter molecule associated as an adduct with an oligonucleotide probe capable of hybridizing with said target nucleic acid sequence.

The present invention primarily embodies 1) imposing a transcription step between the production of an appropriate reporter molecule and the replication event of amplification and 2) uses, if at all, relatively short, stable RNAs as reporter molecules. Necessarily, the replicatability of the replicatable transcripts hereof follows by having disposed within the sequence of said transcripts a sequence that is recognized by replicase enzyme.

The present invention further embodies means for measuring the amount of said detected replicatable transcripts.

In an aspect, the present invention is directed to a method useful for the detection of at least one specific nucleic acid target sequence in a sample containing nucleic acid, comprising hybridizing under suitable conditions an oligonucleotide-promoter/DNA molecule adduct comprising an oligonucleotide probe corresponding in sequence to a segment of said target sequence in a sample containing nucleic acid, and linked thereto a functional length of promoter sequence operably linked to a single- or double-stranded DNA molecule encoding replicatable RNA transcript, eliminating excess, non-hybridized oligonucleotide-promoter/DNA molecule adduct, assaying the number of promoter/DNA molecule sequences associated by hybridization with said target nucleic acid sequence by using it to direct the transcription of said single- or-double-stranded DNA by associating said promoter/DNA molecule sequence with an RNA polymerase, allowing the transcript products to replicate, and detecting the replicated transcripts.

The present invention, in application, embodies the detection of said self-replicated RNA transcripts such as via radio- or chromophore-labeling techniques known per se.

The present invention contemplates the detection of target nucleic acid sequence in a sample wherein said target nucleic acid sequence is associated with characteristics of a genetic or pathogenic disease or condition, and particularly those wherein the nucleic acid sequence is a segment of a human virus or is a segment of a defective gene.

There are a number of human diseases that are either the direct result of a genetic defect or are correlated with the presence of a particular genetic allele. By way of example, the technique described in this application could be used to determine whether or not a given target gene is present in a very small sample of DNA. This would be useful in the prenatal diagnosis of genetic disorders such as hydrops fetalis (absence of α globin DNA) or Lepore hemoglobinopathy (nonhomologous crossing over between δ and β globin genes). The technique could also be used to detect mRNA species. It would be useful, for example, in the diagnosis of Cooley's anemia; a disease characterized by the absence of β globin mRNA. Another potential application is the detection of latent viral infections. DNA from peripheral blood cells could be tested for the presence of HIV-1 (AIDS virus) DNA which has become integrated into the host genome. The technique may also be used to determine the HLA type of a small tissue sample. This would be useful in assessing the genetic predisposition of an individual to disorders such as ankylosing spondylitis and Reiter's syndrome.

The present invention contemplates the use of particular promoters such as the bacteriophage T7 promoter and wherein RNA transcripts are produced using T7 RNA polymerase or use of the SP6 promoter and corresponding SP6 RNA polymerase.

The present invention is also directed to assay systems and kits embodying same, useful for the detection of at least one specific nucleic acid target sequence in a sample containing nucleic acid, comprising detecting self-replicated RNA transcript produced from a DNA molecule encoding same operably linked to a promoter therefor, said promoter and DNA molecule being a reporter molecule associated as an adduct with an oligonucleotide probe capable of hybridizing with said target nucleic acid sequence, and means for hybridizing said probe and utilizing the linked reporter of said hybridized probe to cause transcription of said DNA molecule and thereby to detect and measure said replicatable RNA transcript products therefrom, and by deduction said target sequence.

DETAILED DESCRIPTION OF THE INVENTION

2. GENERAL METHODS AND DEFINITIONS

Reference is made to standard textbooks of molecular biology that contain definitions and methods and means for carrying out basic techniques of the present invention, such as:

DNA probe or primer preparation, including DNA synthesis or isolation of sequences from natural source via restriction enzyme cleavage and the tailoring thereof so as to be suitable as such or when linked to other DNA for use as a primer or probe herein;

preparation of the linked adducts of oligonucleotides and nucleic acids or polypeptides for use in hybridization as oligonucleotide probe/reporter molecule;

hybridization methodology including variations in stringency conditions for producing more or less hybridization certainty depending on the degree of homology of the primer to a target DNA sequence;

identification, isolation or preparation of promoters, or more specifically promoters or sites recognized by bacteriophage DNA-dependant RNA polymerase and bacteriophage RNA-dependant RNA polymerase or in the employment of eukaryotic systems, viral DNA- and RNA-dependent RNA polymerases, for example, adenovirus encoded RNA polymerase and brome mosaic virus RNA polymerase;

identification, isolation or preparation of RNA polymerases capable of recognizing said promoters referred to above;

conditions conducive to the production of RNA transcripts, including so-called transcription-enhancer sequences;

the mechanism and methodology for (induced) replication; and so forth.

See, for example, Maniatis et al., *Molecular Cloning: A Laboratory Manual*, Cold Spring Harbor Laboratory, New York 1982), and the various references cited therein; Hong, *Bioscience Reports* 1, 243 (1981); Cooke et al., *J. Biol. Chem.* 255 6502 (1980); and Zoller et al., *Methods in Enzymology* 100, 468–500 (1983); Crea et al., *Nucleic Acids Res.* 8, 2331 (1980); Narang et al., *Meth. Enzym.* 68, 90 (1979); Beaucage et al., *Tetrahedron Letters* 22, 1859 (1981); Brown et al., *Meth. Enzym.* 68 109 (1979); Caruthers et al., *Meth. Enzym.* 154, 287 (1985); Hitzeman et al., *J. Biol. Chem.* 255, 2073 (1980); Lee et al., *Science* 239, 1288

(1988); Milligan et al., *Nucleic Acids Res.* 15, 8783 (1987); Miller et al., *Virology* 125, 236 (1983), Ahlquist et al., *J. Mol. Biol.* 153, 23 (1981); Miller et al., *Nature* 313, 68 (1985); Ahlquist et al., *J. Mol. Biol.* 172, 369 (1984); Ahlquist et al., *Plant Mol. Biol.* 3, 37 (1984); Ou et al., *PNAS* 79, 5235 (1982); Chu et al., *Nucl. Acids Res.* 14, 5591 (1986); European Patent Application Publn. No. (EPA) 194809; Marsh et al., *Positive Strand RNA Viruses*, p. 327–336, Alan R. Liss (publ.; New York) (1987; Proceedings of UCLA Symposium, 1986); Miller et al., *J. Mol. Biol.* 187, 537 (1986); Stoflet et al., *Science* 239, 491 (1988); Kramer et al., *J. Mol. Biol.* 89, 719 (1974); Saris et al., *Nucl. Acids Res.* 10, 4831 (1982); Bresser et al., *PNAS* 80, 6523 (1983); and Chu et al., *Nucleic Acids Research* 16, 3671 (1988), as well as the references cited therein.

All of the aforecited publications are by this reference hereby incorporated by reference herein.

By the term "promoter" is meant a nucleic acid sequence (naturally occurring or synthetically produced or a product of restriction digest) that is specifically recognized by an RNA polymerase that binds to a recognized sequence and initiates the process of transcription whereby an RNA transcript is produced. It may optionally contain nucleotide bases extending beyond the actual recognition site, thought to impart additional stability toward degradation processes, and may also include additional plus (+) nucleotides contiguous to the transcription initiation site. In principle, any promoter sequence may be employed for which there is a known and available polymerase that is capable of recognizing the initiation sequence. Typical, known and useful promoters are those that are recognized by certain bacteriophage polymerase such as bacteriophage T3, T7 or SP6. See Siebenlist et al., *Cell* 20, 269 (1980). These are but examples of those polymerases that can be employed in the practice of the present invention in conjunction with their associated promoter sequences.

As the promoter is a part of the reporter molecule it is defined, because it exists as a single-stranded version of an otherwise fully operable, classically defined, double-stranded promoter as given immediately above.

The "RNA transcript" hereof is the ribonucleic acid sequence produced after transcription initiation following RNA polymerase recognition of the promoter sequence (See supra). The production of such transcripts is more or less continuous, dependent in part on the amount of polymerase present.

By the term "primer" in the present context is meant a nucleic acid sequence (naturally occurring or synthetically produced or a product of restriction digest) that has sufficient homology with the target sequence such that under suitable hybridization conditions it is capable of hybridizing, that is binding to, the target sequence. A typical primer is at least about 10 nucleotides in length, and most preferably is of approximately 35 or more nucleotide bases in length, and in its most preferred embodiments, it shares identity or very high homology with the target sequence. See, for example, EPA 128042 (publd. 12 Dec. 1984).

The term "operably linked" in particular in connection with the linkage of a promoter sequence within an RNA encoding DNA sequence, refers to its functionality in producing corresponding RNA transcripts when the promoter is recognized by the suitable polymerase—see supra.

The techniques of forming a detection signal such as via radioactive labeling or chromogenic means using a chromogenic susceptible enzyme are also well known and documented in the art. See discussion supra.

A sample on which the assay method of the invention is carried out can be a raw specimen of biological material, such as serum or other body fluid, tissue culture medium or food material. More typically, the method is carried out on a sample which is a processed specimen, derived from a raw specimen by various treatments to remove materials that would interfere with detection of target, such as by causing non-specific binding of affinity molecules. Methods of processing raw samples to obtain a sample more suitable for the assay methods of the invention are well known in the art.

Thus, the method can be carried out on nucleic acid from cells following the colony hybridization method of Grunstein et al, *Proc. Natl. Acad. Sci.* (U.S.A.) 72, 3961 (1975) (see also, U.S. Pat. Nos. 4,358,535 and 4,562,159) or the plaque lift method of Benton et al., *Science* 196, 180 (1977). It can also be carried out on nucleic acids isolated from viroids, viruses or cells of a specimen and deposited onto solid supports (Gillespie et al., *J. Mol. Biol.* 12, 829 (1965)); including solid supports on dipsticks and the inside walls of microliter plate wells. The method can also be carried out with nucleic acid isolated from specimens and deposited on solid support by "dot" blotting (Kafatos et al., *Nucl. Acids Res.* 7, 1541 (1979); White et al., *J. Biol. Chem.* 257, 8569 (1982); Southern blotting (Southern, *J. Mol. Biol.* 98, 503 (1975); "northern" blotting (Thomas, *Proc. Natl. Acad. Sci.* (U.S.A.). 77, 5201 (1980); and electroblotting (Stellwag et al., *Nucl. Acids Res.* 8, 299 (1980)). Nucleic acid of specimens can also be assayed by the method of the present invention applied to water phase hybridization (Britten et al., *Science* 161, 527 (1968)) and water/organic interphase hybridizations (Kohne et al., *Biochemistry* 16, 5329 (1977). Water/organic interphase hybridizations have the advantage of proceeding with very rapid kinetics but are not suitable when an organic phase-soluble linking moiety, such as biotin, is joined to the nucleic acid affinity molecule.

The assay method of the invention can also be carried out on proteins or polysaccharides isolated from specimens and deposited onto solid supports by dot-blotting, by "Western" blotting, or by adsorption onto walls of microliter plate wells or solid support materials on dipsticks.

Still further, the method of the invention is applicable to detecting cellular proteins or polysaccharides on the surfaces of whole cells from a specimen or proteins or polysaccharides from microorganisms immobilized on a solid support, such as replica-plated bacteria or yeast.

Reference herein to bacteriophage Qβ is not limited to any particular variant or mutant or population thereof. Such reference, unless otherwise specifically limited, is to any variant, mutant or population which, upon infection therewith of *E. coli* susceptible to bacteriophage Qβ infection, is capable of causing production of an RNA-dependent RNA-polymerase.

For other phages which, upon infection of bacteria susceptible to infection therewith, produce RNA-dependent RNA polymerases, and associated replicatable RNAs capable of being autocatalytically replicated in vitro, which can be employed in the present invention, see, e.g., Miyake et al., *Proc. Natl. Acad. Sci.* (U.S.A.) 68, 2022 (1971).

The term "linked" herein referring to the moieties of the adduct contemplates both covalent and non-covalent bonding, preferably covalent.

Examples of covalent linkages include, among others, the following:

(a) Linking moiety is a phosphate group and linkage is directly between the phosphate and the 5'-carbon of the 5'-nucleotide of replicative RNA. The phosphate linking moiety, bonded to the 5'-carbon of the 5'-nucleotide of replicative RNA, will usually be involved in covalently joining a replicative RNA directly to the 3'-carbon of the 3'-nucleotide of a nucleic acid affinity molecule or to the 3'-carbon of the 3'-nucleotide of a segment of nucleotides which is a linking moiety considered to be bonded to the 3'-end of a nucleic acid affinity molecule and which is covalently joined, through a phosphate at the 5'-carbon of its 5'-nucleotide, to the 3'-carbon of the 3'-nucleotide of the affinity molecule. The 5'-terminal nucleotide of a replicative RNA can be phosphorylated at the 5'-carbon with T4 polynucleotide kinase by methods known in the art. Affinity molecule, or nucleic acid linking moiety of affinity molecule, can then be connected to the 5'-phosphate of the 5'-nucleotide of replicative RNA by known methods employing T4 RNA ligase. This latter reaction proceeds more efficiently if a ribonucleotide is at the 3'-terminus of the affinity molecule as known in the art, a single ribonucleotide can be attached to the 3'-terminus of a DNA with terminal deoxynucleotidyl transferase.

(b) Linking moiety is biotinyl or iminobiotinyl and linkage is to the 5'-carbon of the 5'-nucleotide of replicative RNA through a spacer group of formula $-NH(CH_2)_{aa}NH(PO_2)O-$, formula $-NH(CH_2)_{bb}SS(CH_2)_{cc}NH(PO_2)O-$, or formula $-HN(CH_2)_{bb}(CO)(NH)(CH_2)_{cc}NH(PO_2)O-$ wherein, in each case, the phosphoramidate group is bonded to the 5'-nucleotide and the amino group to the biotinyl or iminobiotinyl, aa is 2 to 20, and bb and cc are the same or different and are each 2 to 10. Replicative RNA with spacer group of formula $-NH(CH_2)_{aa}NH(PO_2)O-$ can be made following the teaching of Chu and Orgel, *DNA* 4, 327 (1985). Replicative RNA with spacer group of formula $-NH(CH_2)_{bb}SS(CH_2)_{cc}NH(PO_2)O-$ is taught in Example I. Replicative RNA with spacer group of formula $-NH(CH_2)_{bb}(CO)(NH)(CH_2)_{cc}NH(PO_2)O-$ is made by reacting replicative RNA, with group of formula $-O(PO_2)NH(CH_2)_{cc}NH_2$ bonded to the 5'-carbon of the 5'-nucleotide, with an active ester of the aminocarboxylic acid of formula $NH_2(CH_2)_{bb}CO_2H$. Reaction of N-hydroxysuccinimo ester of biotin or iminobiotin to form a biotin-amide or iminobiotin-amide linkage with a primary amino group is known in the art.

(c) An amino group linking moiety linked through a spacer group of formula $-(CH_2)_{aa}(NH)(PO_2)O-$ or $-(CH_2)_{bb}SS(CH_2)_{cc}NH(PO_2)O-$, wherein the phosphoramidate group is linked to the 5'-carbon of the 5'-nucleotide of the replicative RNA and wherein aa, bb and cc are as defined supra. The methods of Chu and Orgel, *DNA* 4, 327 can be employed to prepare such replicative RNAs.

(d) A sulfur linking moiety joined by a spacer group of formula $-(CH_2)_{cc}NH(PO_2)O-$, wherein the phosphoramidate group is bound to the 5'-carbon of the 5'-nucleotide of replicative RNA and cc is as defined above. See Chu and Orgel, *Nucleic Acids Research* 16, 3671 (1988).

Among additional information in the art relating to joining linking moieties to proteins and nucleic acids see, e.g., Dreyer et al., *Proc. Natl. Acad. Sci.* (U.S.A.) 82, 968 (1985); Forster et al., *Nucl. Acids Res.* 13, 745 (1984); Ward et al., European Patent Application Publication No. 0 063 879; Englehardt et al., European Patent Application Publication No. 0 097 373; Alagon et al., *Biochemistry* 19, 4341 (1980); Imam et al., *Cancer Res.* 45, 263 (1985).

The replicated transcripts (RNA) can be detected in a number of different ways:

Detection can be by ultraviolet absorbance of replicated RNA, as, for example, by the method of contact photoprinting (Kutateladze et al., *Anal. Biochem.* 100, 129 (1979)).

By employing a radioactively labeled ribonucleoside-5'-triphosphate in the replication reaction (e.g., $^3$H-labeled or alpha-$^{32}PO_4$-labeled), so that the replicated RNA is radioactive, the replicated RNA can be detected, by any of numerous known procedures, by means of its radioactivity.

Biotin or iminobiotin can be incorporated into replicated RNA, which can then be detected by known techniques with an enzyme-avidin or enzyme-streptavidin adduct, which binds to the RNA-bound biotin and catalyzes production of a conveniently detectable chromogen. Incorporation of biotin or iminobiotin can be accomplished by employing UTP that is biotinylated through a spacer to carbon-5 of the uracil moiety as a substrate for the replicase in the replication reaction. Such UTP's are known compounds. Further, it is known that such UTP's are substrates for Qβ replicase, and that RNAs which include uracils biotinylated through spacer groups joined to the carbon-5 position, due to use of such UTP's in their synthesis, are templates for Qβ replicase catalyzed replication.

RNA resulting from the replication process could also be biotinylated employing photobiotin acetate and then detected, with an avidin-enzyme adduct-chromogenic compound system, like replicated RNA's synthesized with biotinylated UTP in the replication reaction.

RNA resulting from the replication process can be made fluorescent by employing a T4 RNA ligase catalyzed reaction to append nucleotides modified to be fluorescent to the 3'-end of replicative RNA. See Cosstick et al., *Nucl. Acids Res.* 12, 1791 (1984). The fluorescence of the resulting RNA can be employed to detect the RNA by any of several standard techniques.

Among still other methods that can be used to detect replicated RNA are those wherein a reporter substance, that binds specifically with nucleic acid, is added to the system in which the replication has taken place, or to the medium, such as a positively charged support such as ECTEOLA paper, on which replicated RNA has been isolated, and signal from the reporter substance measured. Such substances include: chromogenic dyes, such as "stains all" (Dahlberg et al., *J. Mol. Biol.* 41, 139 (1969); methylene blue (Dingman et al., *Biochemistry* 7, 659 (1968), and silver stain (Sammons et al., *Electrophoresis* 2, 135 (1981); Igloi, *Anal. Biochem.* 134, 184 (1983)); fluorogenic compounds that bind to RNA—for example, ethidium bromide (Sharp et al., *Biochemistry* 12, 3055 (1973); Bailey et al., *Anal. Biochem.* 70, 75 (1976); and fluorogenic compounds that bind specifically to RNAs that are templates for replication by Qβ replicase—for example, a phycobiliprotein (Oi et al., *J. Cell Biol.* 93, 981 (1982); Stryer et al., U.S. Pat. No. 4,520,110) conjugated to the viral subunit of Qβ replicase.

Provided that the concentration of replicase remains above the concentration of template RNA, and that ribonucleoside-5'-triphosphate concentration does not become limiting, the concentration of template RNA will increase exponentially with time during replicase-catalyzed RNA replication. After template RNA concentration equals or exceeds replicase concentration, as long as ribonucleoside-5'-triphosphate concentration does not become limiting, the concentration of template RNA will increase linearly with time. See, e.g., Kramer et al. (1974), supra.

It has been found that, under the conditions for replicase-catalyzed replication, the MDV-1 RNA there exemplified doubled in concentration every 36 seconds, until template concentration exceeded enzyme concentration.

The concentration of template RNA, in a replicase-catalyzed replication reaction system after a given time for reaction, will be related to the initial concentration of template RNA. If, at all times during the replication reaction, the concentration of replicase exceeds that of template (and ribonucleoside-5'-triphosphate concentration does not become limiting), the log of concentration of template RNA at the conclusion of the reaction will be directly proportional to the log of the initial concentration of template (at the start of the reaction). After replicase concentration falls below template concentration, as long as ribonucleoside-5'-triphosphate concentration does not become limiting, the concentration of template at the conclusion of reaction is directly proportional to the log of the initial concentration of template. Further, the time required for a reaction to reach the point at which template concentration equals replicase concentration is proportional to the negative log of the initial concentration of template.

By allowing the replication reaction to proceed for longer times, greater sensitivity can be achieved.

In assays according to the invention, assays are carried out simultaneously, under conditions as nearly alike as possible, on both test samples, which are being tested for analyte, and control samples. As understood in the art, control samples are similar to test samples but are known to contain either no analyte or a known quantity of analyte. A control with no analyte establishes the "background," below which it is not possible to distinguish samples which contain analyte from those which do not. By comparing the amount or concentration of replicated replicative RNA produced in an assay of a test sample with the amount or concentration produced with control samples assayed simultaneously, the presence of analyte in test sample at a level above background can be determined. If control samples with a range of known concentrations of analyte are employed, the concentration of analyte in a test sample can be estimated.

Again, the use of a "replicase" for (autocatalytic) induction of replication of the RNA transcripts of the present invention are generally known in the art. Suitable examples of such replicases that are useful in the present invention include the so-called Qβ virus replicase that recognizes certain nucleic acid sequence sites at both the 3'- and 5'- ends of the given RNA transcript and the so-called brome mosaic virus (BMV) as well as the alpha virus replicases which are thought to recognize nucleic acid sequence sites at the 3' end of a given RNA transcript. These replicases serve to replicate, that is reproduce, the RNA transcripts and complements so as to multiply copies thereof. When such enzyme is present in the reaction locus during the process of transcription, it can be foreseen that the multiple transcripts that are produced during transcription can themselves undergo replication so as to exponentially increase the amount of RNA transcript product.

3. DETAILED DESCRIPTION OF PARTICULARLY PREFERRED EMBODIMENTS

Figure 1:
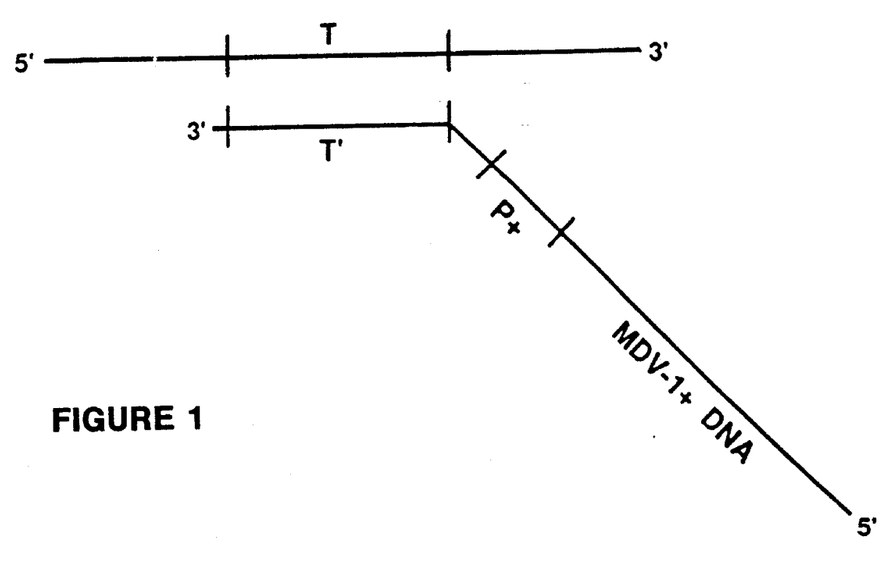
FIG. 1 depicts schematically an aspect of this invention: a target nucleic acid sequence (T) having hybridized thereto a novel oligonucleotide-promoter/DNA molecule adduct hereof, the oligonucleotide moiety (T') being linked to the optionally cleavable promoter/DNA molecule (P+/MDV–1+DNA) (depicted as single-stranded).

The oligonucleotide adduct contains 1) a complement sequence of the target sequence, and 2) the appropriate strand of a promoter sequence and DNA encoding replicative RNA. When moiety 2) is released from its hybridized partner moiety 1) and is associated wit hits complement sequence, RNA polymerase will initiate transcription with detection and measurement of replicated transcript products.

Alternatively the roll of the MDV1 DNA and the negative strand of the promoter may be reversed. Probing in then carried out with the MDV1 P+ DNA sequence. The assay solution would include the P− sequence or the P− sequence attached to the negative strand of MDV1 DNA, in this instance.

4. EXAMPLES

Reference Example 1

The three techniques depend on the use of T7 RNA polymerase and Qβ RNA polymerase to amplify a signal generated by successful target hybridization events. T7 RNA polymerase is a DNA-dependent RNA polymerase that has the following useful properties:

(1) it initiates specifically at sites that lie adjacent to the T7 promoter;

(2) once initiation has occurred, the enzyme can operate on either single- or double- stranded templates;

(3) the enzyme has a high turnover rate, producing 200–1200 moles of RNA transcript per mole of DNA template;

(4) the gene for T7 RNA polymerase has been cloned, making it relatively straightforward to prepare very large amounts (2–10 MU) of the enzyme. All class III (high efficiency) promoters of the T7 vital genome have a common 20 base-pair sequence from −17 to +3:

3'-ATTATGCTGAGTGATATCCC-5'

5'-TAATACGACTCACTATAGGG-3'

Beyond position +3 the template may exist as a single strand without adversely affecting transcription efficiency. Synthesis begins with the sequence GGG and proceeds in the 5'→3' direction. The template is designed such that the product of transcription is the (+) strand of MDV-1RNA. MDV-1 (+) RNA contains 221 nucleotides, beginning with the sequence GGG at its 5' end. It in turn serves as an ideal substrate for Qβ RNA polymerase, an RNA-dependent RNA polymerase which caries out autocatalytic amplification of its substrate RNA. Combining the T7 RNA polymerase system with the Qβ RNA polymerase system provides an extremely powerful tool for amplifying the signal generated by a rare molecular event.

Example 2

The target sequence 5'-GTTGTGTGGAATTGTG-3' (T) which is part of the sequence of the M13mp8 (+) strand DNA is detected. T', the complement of T, is linked to the positive strand of the promoter which is coupled to the 221 nucleotide sequence that codes for MDV-1 RNA. It uses the general principle of the invention to detect T by detecting the production of MDV-1 RNA produced in a suitable assay.

The complement of the target (probe) 5'-CACAATTCCACACAAC-3' (sequence 1) can be synthesized by the solid-phase phosphoamidite method, using a DNA synthesizer.

The positive strand of the promoter 3'-ATTATGCTGAGTGATATCCC-5' (sequence 2) and the 221 nucleotide sequence which codes for MDV-1 RNA (sequence 3) are obtained from a known plasmid containing the T7 promoter operably linked to MDV-1 DNA by digestion with a suitable restriction enzyme. Sequence 1 is joined to sequence 2/3 using, T4 DNA ligase in the presence of a short oligodeoxynucleotide template that spans the ligation junction, to form the probe. Alternatively, the probe can be prepared using the cleavable disulfide bond linkage to form the following adduct:

3'-CAACACACCTTAACAC-5'-P-CH$_2$CH$_2$-SS-CH$_2$CH$_2$-5'-P-(MDV-1+DNA)-CCCTATAGTGAGTCG-TATTA-3', as described (Chu et al, *Nucleic Acids Research*, 16, 3671 (1988). The sequences 1 and 2/3 above are converted to the 5'-phosphate derivatives using polynucleotide kinase and ATP. The 5'-phosphate derivatives (0.1–10 ODU) are converted to the 5'-cystamine derivatives by treatment with 0.1M 1-methylimidazole, 0.15M 1-ethyl-3,3-dimethylaminopropyl carbodiimide and 0.5M cystamine at pH 7 and 50° C. for 2 hours. The 5'-cystamine derivatives are purified either by HPLC on RPC-5 or denaturing gel electrophoresis.

A mixture containing 1 μM of the 5'-cystamine derivative of sequence 2/3 and 5–8 μM of the 5'-cystamine derivative of sequence 1 is treated with 5 mM DTT in TRIS-EDTA buffer at pH 7.2 for 1 hour at room temperature. The reaction mixture is then dialyzed against buffer containing 0.1 mM DTT, 1 mM Tris and 0.1 mM EDTA at pH 7.2 for 30 mins, and against fresh buffer containing 1 mM Tris and 0.1 mM EDTA at pH 7.2 for a further 30 mins. The mixture is then concentrated, if necessary in a speed-vac concentrator and the probe-promoter/MDV-1 adduct purified by gel electrophoresis.

Preparation of Target Sample

M13mp8DNA (+) strand DNA (7229 bases), 1 fg, 10 fg, 100 fg, 1 pg, 10 pg, 100 pg ($4 \times 10^{-7}$ fmole–$4 \times 10^{-5}$ pmoles) is diluted to 200 μl to give a final solution containing 10 mM Tris, 1 mM EDTA, 100 mM NaCl at pH 7.5. Then 20 μl of 3M NaOH are added and the solution is incubated for 30 mins at 60°–70° C. After cooling, the solution is neutralized with 200 μl of 2M ammonium acetate pH 7.0. The DNA is slot-blotted onto nitrocellulose paper that has been pre-wetted with water and mM ammonium acetate using a manifold slot blotter. The paper is then baked in a vacuum over at 80° C. for 1 hour.

Hybridization and Release

The nitrocellulose blots are pre-hybridized for 1 hour at 30° C. in hybridization buffer (900 mM NaCl, 6 mM EDTA, 90 mM Tris pH 7.5, 0.1% SDS) containing 100 μg/ml randomly cleaved RNA. Hybridization with 1 ng/ml of the probe-promoter/MDV-1 adduct is then carried out at 45° C. for 1 hour. The blots are then washed twice with buffer containing 180 mM NaCl at room temperature and again with buffer containing 18 mM NaCl at 30° C.

The probe-promoter/MDV-1 adduct linked by phosphodiester bonds will be released from the target slots in 30 μl boiling buffer, cooled at room temperature for 15 mins. The probe linked to the promoter/MDV-1 adduct by disulfide bonds will be released by incubation of the target slot with 30 μl of 10 mM DDT in Tris-EDTA buffer at 37° C. for 1 hour.,

Hybridization of the Released Promoter/MDV-1

The released DNA, which contains the plus strand of the T7 promoter and the 221 nucleotide sequence that codes for MDV-1 RNA, serves as a reporter for successful target hybridization events. This DNA is in turn hybridized to a single-stranded DNA molecule which contains the minus (−) strand of the T7 promoter optionally, the released DNA can be hybridized to a single-stranded DNA molecule that contains both the minus strand of the T7 promoter and the complement of the 221-nucleotide sequence that codes for MDV-1 RNA. Hybridization occurs in a 40 μl volume which contains 1 pmole (~100 ng) T7 minus promoter DNA, 12 mM $MgCl_2$, 2 mM spermidine, and 50 mM Tris (pH 7.5). This mixture is heated to 65° C. for 5 min and then cooled to 30° C. over 5–10 min. 20 μg (~100U) T7 RNA polymerase, 0.5 μg Qβ RNA polymerase, 12 mM $MgCl_2$, 2 mM spermidine, 10 mM DTT, 50 mM Tris (pH 7.5), and 1 mM each of the four NTPs is added, bringing the total volume to 60 μl. The combined mixture is incubated at 37° C. for 20 min, and then assayed for the production of MDV-1 RNA.

Detection of Replicated RNA

The amount of RNA is determined by its intrinsic UV absorbance (e.g. as by the contact photoprinting method of Kutateladze et al., *Anal. Biochem.* 100, 129 (1979)). Alternatively, the RNA is visualized on ETEOLA paper. Aliquots (of equal volume) of replication reaction are transferred with 13, 48 or 96-fingered aliquotter to sheets of diethylaminoethyl cellulose paper. The sheets are then washed at room temperature in a solution of 200 mM NaCl, 300 mM ammonium acetate pH 6 to remove ribonucleosides not incorporated into RNA. The sheets are then stained with 0.3 μg/ml of ethidium bromide. (Sharp et al., *Biochemistry* 12, 3055 (1973); Bailey et al., *Anal. Biochem* 70, 75 (1976).

Finally the fluorescence from individual blots is measured by any of several known techniques. Fluorescence intensity from a stained blot above that from control blots indicates the presence of analyte. Other staining materials can be employed in place of ethidium bromide. These include methylene blue (Dingman and Peacock, *Biochemistry* 7, 659 (1968)), silver stain (Sammons, et al., *Electrophoresis* 2, 135 (1981)) or phycobiliprotein Qβ replicase conjugate (Oi et al., *J. Cell Biol.* 93, 981 (1982)).

Example 3

Rubella antibody is detected in a patient with recent exposure to rubella antigen. Microliter wells coated with rubella antigen are incubated for 3 hours at room temperature with 50 μl aliquots per well of 1:10, 1:30, 1:100, 1:300, 1:1000, and 1:3000 dilutions of IgG isolated from the patient. Dilutions are prepared with 5% horse serum in phosphate-buffered saline. The plates are then thoroughly washed with Tween 20-NaCl. To each well is then added 50 μl of a solution containing 1 μg/ml of anti-rubella IgG linked by disulfide bonds to the plus strand of the promoter/MDV-1(+). After 2 hours' incubation at room temperature, the plates are washed 3 times with NaCl-Tween 20. A solution of 30 μl of 100 mM DDT in Tris-EDTA Buffer is then added to the wells and incubated at room temperature for 1 hour. The released plus strand of the promoter/MDV-1 is then assayed as described in Example 2.

The synthesis of the anti-rubella IgG-promoter/MDV-1 adduct linked by disulfide bonds is carried out as described in U.S. Ser. No. 852,692, supra. Anti-rubella IgG is first thiolated with imino-thiolane and then reacted with the 5'-(2-pyr)-SS-P-MDV-1(+)DNA-plus strand promoter to give the disulfide linked adduct:

IgG-SS-$CH_2CH_2$-P-5'-MDV-1-promoter

200 μg of rubella anti-IgG is reacted with 1 mM iminothiolane in buffer containing 60 mM triethylamine, 7 mM phosphate, 100 mM NaCl and 1 mM EDTA at pH 8 and 0° C. for 1 hour. (Blattler et al, *Biochemistry* 24, 1517 (1985). The thiolated antibody containing 1 mole of thiol per mole of IgG is separated from unreacted iminothiolane by gel filtration and stored under nitrogen.

The 5'-cystamine adduct of MDV-1(+)DNA-plus strand promoter (0.01–1.0 ODU) is treated with 5 mM DDT in 10 μl of Tris-EDTA buffer pH 7 for 1 hour at room temperature. 40 μl of a 3 mM solution of 2,2'-pyridyl disulfide is then added. After 1 hour at room temperature the 5'-(2-pyr)-SS-MDV-1(+)DNA-plus strand promoter is purified by gel electrophoresis.

400 μl of a solution containing 0.01–1.0 ODU of the 5'-(2-pyr)-SS-P-MDV-1(+)DNA-plus strand promoter and 1 μM of the thiolated anti rubella IgG is dialyzed against buffer containing 1 mM NaCl, 1 mM Tris and 0.1 mM EDTA at pH 7.2 for 1 hour. The solution is then concentrated to 10 μl in a speed-vac concentrator, and allowed to stand overnight at room temperature, It is then applied to a DEAE column. Unreacted IgG is eluted with 50 mM Tris at pH 7, and the IgG-MDV-1(+)DNA-plus strand promoter adduct is eluted with the same buffer containing 0.25M NaCl. Unreacted oligonucleotide can be eluted with buffer containing 0.5M NaCl.

The foregoing description details more specific methods that can be employed to practice the present invention and represents the best mode contemplated. However detailed the foregoing may appear in text, it should not be construed as limiting the overall scope hereof; rather, the ambit of the present invention is to be governed only by the lawful construction of the appended claims.

What is claimed is:

1. An adduct for detecting a target, which adduct comprises:
   (a) a probe moiety capable of specifically forming a complex with said target; linked to
   (b) a single-stranded DNA moiety comprising a promoter sequence which recognizes and binds to a DNA-dependent RNA polymerase when hybridized to a nucleic acid sequence complementary thereto operably linked to a DNA template sequence encoding an RNA transcript replicatable by an RNA-dependent RNA polymerase.

2. An adduct according to claim 1, wherein the probe moiety is capable of specifically forming a complex with a polysaccharide.

3. An adduct according to claim 1, wherein the probe moiety is capable of specifically forming a complex with a protein.

4. An adduct according to claim 1, wherein the probe moiety is an antibody.

5. An adduct according to claim 3, wherein the probe moiety is an antibody.

6. An adduct according to claim 1, wherein the promoter sequence in the DNA moiety is positioned 3' to the DNA template sequence in the DNA moiety.

7. An adduct according to claim 1, wherein the DNA-dependent RNA polymerase is T7 RNA polymerase.

8. An adduct according to claim 1, wherein the DNA-dependent RNA polymerase is SP6 RNA polymerase.

9. An adduct according to claim 1, further comprising a single-stranded nucleic acid molecule containing a nucleic acid sequence complementary to the promoter sequence hybridized to the promoter sequence.

10. A method for detecting the presence of a target in a sample, which method comprises:
    (a) contacting the sample with the adduct of claim 1 under conditions which would permit the probe moiety of the adduct to specifically form a complex with the target if present in the sample;
    (b) removing any uncomplexed adduct from the sample;
    (c) contacting the sample with a single-stranded nucleic acid molecule comprising a nucleic acid sequence which is complementary to the promoter sequence of the DNA moiety of the adduct under conditions permitting the nucleic acid sequence to hybridize with the promoter sequence;
    (d) contacting the sample with a DNA-dependent RNA polymerase under suitable conditions so as to produce RNA transcripts, thereby producing RNA transcripts from the DNA template sequence of the DNA moiety of any of the adduct remaining in the sample;
    (e) incubating the sample with an appropriate RNA-dependent RNA polymerase under suitable conditions so as to produce complementary single-stranded RNA molecules from any RNA transcripts so produced in step (d);
    (f) thereafter simultaneously and repeatedly contacting the sample with the appropriate RNA-dependent RNA polymerase under conditions permitting simultaneous and repeated synthesis of RNA copies having the same sequence as the RNA transcripts in step (d) and RNA copies having the same sequence as complementary single-stranded RNA molecules in step (e); and
    (g) detecting any RNA copies so produced, so as to thereby detect the presence of the target in the sample.

11. The method of claim 10, further comprising measuring the RNA copies detected in step (g) in a standardized manner for detecting an RNA molecule so as to measure the amount of target contained in the sample.

12. The method of claim 10, wherein the detecting in step (g) comprises:
    (i) labeling the RNA copies with a detectable marker; and
    (ii) detecting the marker on the RNA copies so labeled.

13. The method of claim 12, wherein the detectable marker is selected from the group consisting of a radioactive substance, a chromophore, and a fluorophore.

14. A method for detecting the presence of a target in a sample, which method comprises:
    (a) contacting the sample with the adduct of claim 9 under conditions which would permit the probe moiety of the adduct to specifically form a complex with the target if present in the sample;
    (b) removing any uncomplexed adduct from the sample;
    (c) contacting the sample with a DNA-dependent RNA polymerase under suitable conditions so as to produce RNA transcripts, thereby producing RNA transcripts from the DNA template sequence of the DNA moiety of any of the adduct remaining in the sample;
    (d) incubating the sample with an appropriate RNA-dependent RNA polymerase under suitable conditions so as to produce complementary single-stranded RNA molecules from any RNA transcripts so produced in step (c);
    (e) thereafter simultaneously and repeatedly contacting the sample with the appropriate RNA-dependent RNA polymerase under conditions permitting simultaneous and repeated synthesis of RNA copies having the same sequence as the RNA transcripts in step (c) and RNA copies having the same sequence as complementary single-stranded RNA molecules in step (d); and
    (f) detecting any RNA copies so produced, so as to thereby detect the presence of the target in the sample.

15. The method of claim 14, further comprising measuring the RNA copies detected in step (f) in a standardized manner for detecting an RNA molecule so as to measure the amount of target contained in the sample.

16. The method of claim 14, wherein the detecting in step (f) comprises:

(i) labeling the RNA copies with a detectable marker; and (ii) detecting the marker on the RNA copies so labeled.

17. The method of claim 16, wherein the detectable marker is selected from the group consisting of a radioactive substance, a chromophore, and a fluorophore.

18. A kit for detecting a target in a sample, which kit comprises the adduct of claim 1.

19. A kit according to claim 18, further comprising a single-stranded nucleic acid molecule comprising a nucleic acid sequence complementary to the promoter sequence of the DNA moiety of the adduct, A DNA-dependent RNA polymerase capable of transcribing the DNA template sequence of the DNA moiety of the adduct, and an RNA-dependent RNA polymerase capable of replicating RNA transcripts produced by transcribing the DNA template sequence of the DNA moiety of the adduct.

20. A kit for detecting a target in a sample, which kit comprises the adduct of claim 9.

21. A kit according to claim 20, further comprising a DNA-dependent RNA polymerase capable of transcribing the DNA template sequence of the DNA moiety of the adduct and an RNA-dependent RNA polymerase capable of replicating RNA transcripts produced by transcribing the DNA template sequence of the DNA moiety of the adduct.

22. A kit for preparing an adduct for detection of a target, which kit comprises a probe moiety capable of specifically forming a complex with said target, a DNA moiety comprising a promoter sequence which recognizes and binds to a DNA-dependent RNA polymerase when hybridized to a nucleic acid sequence complementary thereto operably linked to a DNA template sequence encoding an RNA transcript replicatable by an RNA-dependent RNA polymerase, and a means for linking said probe moiety to said DNA moiety.

23. A kit according to claim 22, wherein the probe moiety is an antibody.

* * * * *